(12) United States Patent
Jacob et al.

(10) Patent No.: US 6,610,703 B1
(45) Date of Patent: Aug. 26, 2003

(54) METHOD FOR TREATMENT OF GLYCOLIPID STORAGE DISEASES

(75) Inventors: Gary S. Jacob, St. Louis, MO (US); Frances M. Platt, Oxford (GB); Terry D. Butters, Oxford (GB); Raymond A. Dwek, Oxford (GB)

(73) Assignees: G.D. Searle & Co., Chicago, IL (US); Oxford University, Oxford (GB)

( * ) Notice: Subject to any disclaimer, the term of this patent is extended or adjusted under 35 U.S.C. 154(b) by 0 days.

(21) Appl. No.: 09/453,754

(22) Filed: Dec. 2, 1999

Related U.S. Application Data

(60) Provisional application No. 60/111,683, filed on Dec. 10, 1998.

(51) Int. Cl.[7] .................... A61P 25/00; A61K 31/445
(52) U.S. Cl. ............................................. 514/315
(58) Field of Search ............................... 514/315

(56) References Cited

U.S. PATENT DOCUMENTS

| | | | |
|---|---|---|---|
| 5,030,638 A | 7/1991 | Partis et al. | 514/315 |
| 5,472,969 A | 12/1995 | Platt et al. | 514/315 |
| 5,786,368 A | 7/1998 | Platt et al. | 514/315 |
| 5,798,366 A | 8/1998 | Platt et al. | 514/315 |
| 5,801,185 A | 9/1998 | Platt et al. | 514/315 |

FOREIGN PATENT DOCUMENTS

| | | | |
|---|---|---|---|
| EP | 0 913770 | 2/1986 | C07D/211/46 |
| WO | WO98/02161 | 1/1998 | |

OTHER PUBLICATIONS

Platt, et al., J. Biol. Chem., vol. 269, No. 11, pp. 8362–8365 (1994).
Beutler, Proc. Natl. Acad. Sci. USA 90, 5384–5390 (1993.
Dale & Beutler, id. 73, 4672–4674 (1976).
Beutler, Science 256, 794–799 (1992).
Platt et al., J. Biol. Chem. 269, 8362–8365 (1994).
Block et al., Nature Medicine 4, 610–614 (1998).

*Primary Examiner*—Edward J. Webman
(74) *Attorney, Agent, or Firm*—Scott J. Meyer

(57) ABSTRACT

A novel method is disclosed for the treatment of a patient affected with Gaucher's disease or other such glycolipid storage diseases. The method comprises administering to said patient a therapeutically effective amount of a long-chain N-alkyl derivative of deoxynojirimycin to alleviate or inhibit the glycolipid storage disease. The long-chain alkyl group has from nine to about 20 carbon atoms and preferably is nonyl or decyl.

12 Claims, 14 Drawing Sheets

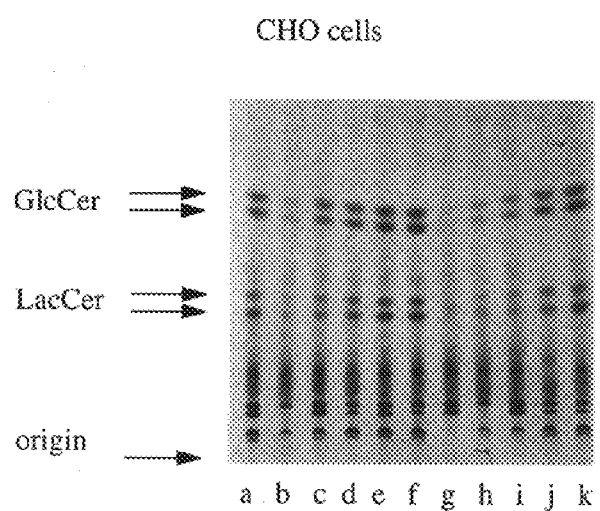
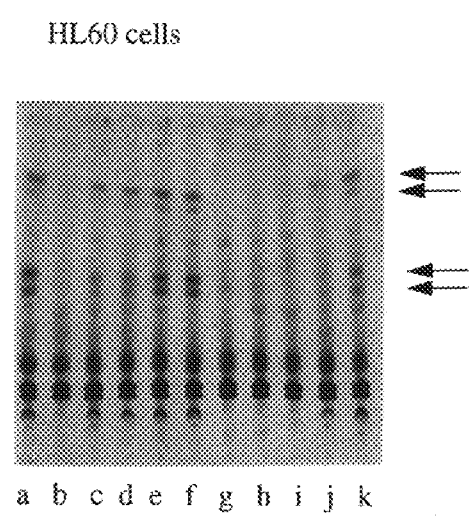
FIG. 1A  CHO cells
FIG. 1B  HL60 cells

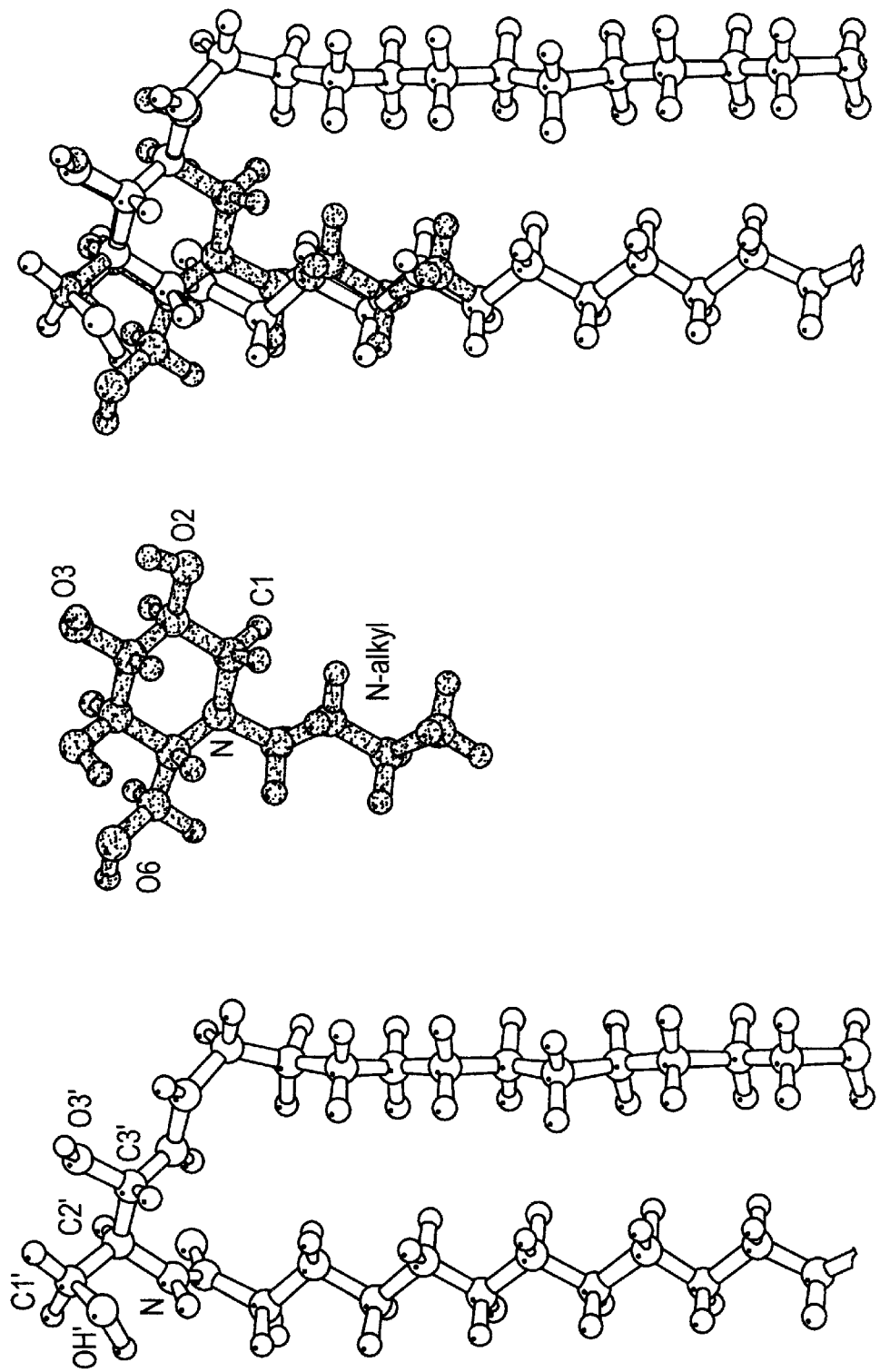

N-alkylated deoxynojirimycin

R=

$-CH_2CH_2CH_2CH_3$
$-CH_2CH_2CH_2CH_2CH_3$
$-CH_2CH_2CH_2CH_2CH_2CH_3$
$-(CH_2)_6CH_3$
$-(CH_2)_6CH_2CH_3$
$-(CH_2)_6CH_2CH_2CH_3$
$-(CH_2)_6CH_2CH_2CH_2CH_3$
$-(CH_2)_6CH_2CH_2CH_2CH_2CH_2CH_3$
$-CH_2(CH_2)_9CHCH(CH_2)_3CH_3$
$-CH_2(CH_2)_{11}CHCH(CH_2)_3CH_3$

Inhibitory Constants of C4-C18 DNJ Analogues for Ceramide Glucosyltransferase and α-Glucosidase

| Chain length | CerGlcT (IC$_{50}$, μM) | α-Glucosidase (IC$_{50}$, μM) |
|---|---|---|
| 4  | 34.4 | 0.57 |
| 5  | 26.8 |      |
| 6  | 23.8 |      |
| 8  | 16.8 |      |
| 9  | 7.4  |      |
| 10 | 3.1  | 0.48 |
| 12 | 5.2  |      |
| 16 | 3.4  |      |
| 18 | 4.1  |      |

C4-C18 DNJ Analogue Uptake in MDBK Cells

METHOD FOR TREATMENT OF GLYCOLIPID STORAGE DISEASES

This is a Continuation-in-part of Application Ser. No. 60/111,683, filed Dec. 10, 1998.

BACKGROUND OF THE INVENTION

The present invention relates to a method for the treatment of Gaucher's disease and other glycolipid storage diseases.

Gaucher's disease is a glycolytic storage disease caused by a genetic deficiency in activity of the catabolic enzyme beta-glucocerebrosidase. Beutler, *Proc. Natl. Acad. Sci. USA* 90, 5384–5390 (1993). Manifestations of this disease are impaired hematopoiesis, bone fractures, a thinning of the bone cortex and massive enlargement of the spleen and liver.

In recent years, several therapies have been proposed for the treatment of Gaucher's disease. An early therapeutic approach involved replacement of the deficient enzyme. See, for example, Dale and Beutler, *Proc. Natl. Acad. Sci. USA* 73, 4672–4674 (1976); Beutler et al., *Blood* 78, 1183–1189 (1991); and Beutler, *Science* 256, 794–799 (1992).

Leading commercial products for enzyme replacement are CEREDASE (glucocerebrosidase), which is derived from human placental tissues, and CEREZYME (recombinant human glucocerebrosidase), both of which are produced by Genzyme Corp. See, for example, U.S. Pat. Nos. 3,910,822; 5,236,838; and 5,549,892.

Conjugates of the glucocerebrosidase enzyme with polyethylene glycol (PEG) have also been advanced by Enzon Inc. for treatment of Gaucher's disease. See, for example, U.S. Pat. Nos. 5,705,153 and 5,620,884.

Still another approach for treatment of the disease is gene therapy, which involves an ex vivo gene transfer protocol.

Another recent approach involves administration of the totally synthetic drugs, N-butyldeoxynojirimycin and N-butyldeoxygalactonojirimycin, as described, respectively, by Platt et al., *J. Biol. Chem.* 269, 8362–8365 (1994); *Id.* 269, 27108–27114 (1994). See also, U.S. Pat. Nos. 5,472,969; 5,786,368; 5,798,366; and 5,801,185.

N-butyldeoxynojirimycin (N-butyl-DNJ) and related N-alkyl derivatives of DNJ are known inhibitors of the N-linked oligo-saccharide processing enzymes, α-glucosidase I and II. Saunier et al., *J. Biol. Chem.* 257, 14155–14161 (1982); Elbein, *Ann. Rev. Biochem.* 56, 497–534 (1987). As glucose analogs, they also have potential to inhibit glycosyltransferases. Newbrun et al., *Arch. Oral Biol.* 28, 516–536 (1983); Wang et al., *Tetrahedron Lett.* 34, 403–406 (1993). Their inhibitory activity against the glycosidases has led to the development of these compounds as antihyperglycemic agents and as antiviral agents. See, e.g., PCT Int'l. Appln. WO 87/030903 and U.S. Pat. Nos. 4,065,562; 4,182,767; 4,533,668; 4,639,436; 5,011,829; and 5,030,638.

In particular, N-butyl-DNJ has been developed as an inhibitor of human immunodeficiency virus (HIV) as described by Karpas et al., *Proc. Nat'l. Acad. Sci. USA* 85, 9229–9233 (1988), U.S. Pat. No. 4,849,430; and as an inhibitor of hepatitis B virus (HBV) as described by Block et al., *Proc. Natl. Acad. Sci. USA* 91, 2235–2239 (1994), PCT Int'l. Appln. WO 95/19172.

BRIEF DESCRIPTION OF THE INVENTION

In accordance with the present invention, a novel method is provided for the treatment of a patient affected with Gaucher's disease or other such glycolipid storage diseases. The method comprises administering to said patient a therapeutically effective amount of a long-chain N-alkyl derivative of 1,5-dideoxy-1,5-imino-D-glucitol having from nine to about 20 carbon atoms in the alkyl chain. The N-alkyl substituent thus can be, e.g, nonyl, decyl, undecyl, dodecyl, tetradecyl, hexadecyl, cis-11-hexadecenyl, octadecyl, cis-13-octadecenyl, and eicosyl. A therapeutically effective amount is meant an amount effective in alleviating or inhibiting Gaucher's disease or other such glycolipid storage diseases in said patient.

The alkyl group in these long-chain N-alkyl-DNJ compounds preferably contains nine to ten carbon atoms (i.e., nonyl and decyl). A most preferred compound is N-nonyl-1.5-dideoxy-1,5-imino-D-glucitol, also known as the N-non erivative of deoxynojirimycin (DNJ), which also is abbreviated herein as N-nonyl-DNJ.

In the field of general organic chemistry, the long-chain alkyl groups are known to provide more hydrophobic properties to compounds than are the short-chain alkyl groups. That is, solubility with water decreases with increase in chain length and decrease in temperature. For example, at 46° C., caproic acid (short-chain hexyl group) dissolves 10% by weight of water, whereas stearic acid (long-chain octadecyl group) dissolves only 0.92% even at the higher temperature of 69° C. *Bailey's Industrial Oil and Fat Products*, ed. Daniel Swern, 3d ed. 1964, p. 126.

The long-chain N-alkyl derivatives of DNJ are known amino-sugar compounds. They were originally described as members of a group of short-chain and long-chain N-alkyl derivatives of DNJ having both glucosidase I inhibitory activity and antiviral activity, although no data on the long-chain N-alkyl derivatives was disclosed. See, e.g., DE 3,737,523, EP 315,017 and U.S. Pat. Nos. 4,260,622; 4,639,436; and 5,051,407.

In another early study, although N-alkylation of the base DNJ reduced the concentration required for 50% inhibition of glucosidase I, the inhibitory activity was reduced as the length of the N-alkyl chain was increased from N-methyl to N-decyl according to Schweden et al., *Arch. Biochem. Biophys.* 248, 335–340, at 338 (1986).

As far as the antiviral activity of the amino-sugar compounds against any particular virus is concerned, the activity of any specific analog cannot be predicted in advance. For example, in biologic tests for inhibitory activity against the human immunodeficiency virus (HIV), slight changes in the structure of the N-substituent were shown to have pronounced effects upon the antiviral profile as reported by Fleet et al., *FEBS Lett.* 237, 128–132 (1988). As disclosed in U.S. Pat. No. 4,849,430, the N-butyl derivative of DNJ was unexpectedly found to be more than two log orders more effective as an inhibitor of HIV than the N-methyl analog and three log orders more effective than the N-ethyl analog.

In another study of N-alkyl derivatives of DNJ for activity against glycolipid biosynthesis, the N-hexyl derivative of DNJ required a dose of 0.2 mg/ml, whereas the corresponding N-butyl analog required a dose of only 0.01–0.1. On the other hand, the N-methyl analog was inactive. Thus, it was believed that effective carbon chain length of the N-alkyl group for this activity ranged from 2 to 8 according to U.S. Pat. No. 5,472,969. No disclosure was made therein concerning the N-nonyl or other long-chain N-alkyl derivatives of DNJ.

N-nonyl-DNJ has been reported to be effective as an inhibitor of the Hepatitis B virus (HBV) based on inhibition of alpha-glucosidases in the cellular endoplasmic reticulum (ER) according to Block et al., *Nature Medicine* 4(5) 610–614 (1998).

The effectiveness of the long-chain N-alkyl derivatives of DNJ in the method of the invention for treatment of Gaucher's disease and other such glycolipid storage diseases is illustratively demonstrated herein by inhibitory activity of N-nonyl and N-decyl DNJs against glycolipid biosynthesis in Chinese hamster ovary (CHO) cells and human myeloid (HL-60) cells.

CHO cells are known glycoprotein-secreting mammalian cells. A typical CHO cell line is CHO-K1 which is available to the public from the American Type Culture Collection, Bethesda, Md. under accession number ATCC CCL 61.

HL-60 cells are human promyelocytic cells described by Collins et al., *Nature* 270, 347–349 (1977). They are also readily available from the American Type Culture Collection under accession number ATCC CCL 240.

Effective activity of N-nonyl-DNJ also is further illustratively demonstrated herein in conventional bovine kidney cells (e.g., MDBK, ATCC CCL 22) and hepatoma cells (e.g., HepG2, ATCC HB 8065).

The unpredictability of the N-nonyl-DNJ against glycolipid biosynthesis is demonstrated herein by its inhibitory activity in the foregoing two cell lines. The N-nonyl-DNJ was unexpectedly found to be from about ten- to about twenty-fold better in the CHO cells and about four hundred times better in the HL-60 cells than N-butyl-DNJ at equivalent concentrations. The N-decyl-DNJ was demonstrated to be an effective inhibitor in HL-60 cells at 50 times lower concentrations than N-butyl-DNJ.

The N-nonyl-DNJ also exhibits a more dramatic difference than N-butyl-DNJ in uptake which permits its use at a substantially lower level. In tests of organ distribution, the N-nonyl-DNJ was taken up five times better into the brain than N-butyl-DNJ. Thus, the N-nonyl-DNJ is believed to be a substantially better compound than N-butyl-DNJ for treating glycolipid storage disorders which involve the non-systemic side.

N-nonyl-DNJ and N-decyl-DNJ can be conveniently prepared by the N-nonylation or N-decylation, respectively, of 1,5-dideoxy-1,5-imino-D-glucitol (DNJ) by methods analogous to the N-butylation of DNJ as described in Example 2 of U.S. Pat. No. 4,639,436 by substituting an equivalent amount of n-nonylaldehyde or n-decylaldehyde for n-butylraldehyde. The starting materials are readily available from many commercial sources. For example, DNJ is available from Sigma, St. Louis, Mo. n-Nonylaldehyde, also known as 1-nonanal or pelargonaldehyde, and n-decylaldehyde, also known as decanal, are commercially available from Aldrich, Milwaukee, WI. It will be appreciated, however, that the method of the invention is not limited to any particular method of synthesis of the N-nonyl-DNJ, N-decyl-DNJ, or other long-chain N-alkyl derivatives of DNJ.

The N-nonyl-DNJ, N-decyl-DNJ, and other long-chain N-alkyl derivatives of DNJ, can be used for treatment of patients afflicted with Gaucher's disease and other glycolipid storage diseases by conventional methods of administering therapeutic drugs. Thus, the active compound is preferably formulated with pharmaceutically acceptable diluents and carriers. The active drug can be used in the free amine form or the salt form. Pharmaceutically acceptable salt forms are illustrated, e.g., by the HCl salt. The amount of the active drug to be administered must be an effective amount, that is, an amount which is medically beneficial against Gaucher's disease or other glycolipid storage disease but does not present adverse toxic effects which overweigh the advantages that accompany its use. It would be expected that the adult human daily dosage would normally range from about 0.1 to about 1000 milligrams of the a active compound. The preferable route of administration is orally in the form of capsules, tablets, syrups, elixirs, gels and the like, although parenteral administration also can be used.

Suitable formulations of the active compound in pharmaceutically acceptable diluents and carriers in therapeutic dosage form can be prepared by the person skilled in the art by reference to general texts and treatises in the pharmaceutical field such as, for example, *Remington's Pharmaceutical Sciences*, Ed. Arthur Osol, 16 ed., 1980, Mack Publishing Co., Easton, Pa. and 18th ed., 1990.

Other glycolipid storage diseases to which the method of the invention is directed are, e.g., Tay-Sachs disease, Sandhoff disease, Fabry disease, GM1 gangliosidosis and fucosidosis.

DETAILED DESCRIPTION OF THE INVENTION

While the specification concludes with claims particularly pointing out and distinctly claiming the subject matter regarded as forming the invention, it is believed that the invention will be better understood from the following preferred embodiments of the invention taken in conjunction with the accompanying drawings.

BRIEF DESCRIPTION OF THE DRAWINGS

FIG. 1 shows thin layer chromatography of (a) CHO and (b) HL-60 treated cells. Cells were cultured for four days in the presence of radiolabelled palmitic acid and the following concentrations of compound:

a) control, no compound
b) 50 $\mu$M NB-DNJ
c) 5 $\mu$M NB-DNJ
d) 2.5 $\mu$M NB-DNJ
e) 0.25 $\mu$M NB-DNJ
f) 0.025 $\mu$M NB-DNJ
g) 50 $\mu$M NN-DNJ
h) 5 $\mu$M NN-DNJ
i) 2.5 $\mu$M NN-DNJ
j) 0.25 $\mu$M NN-DNJ
k) 0.025 $\mu$M NN-DNJ After extraction the radioactively labelled glycolipids were separated by TLC and visualized by radioautography.

Figure 2A:
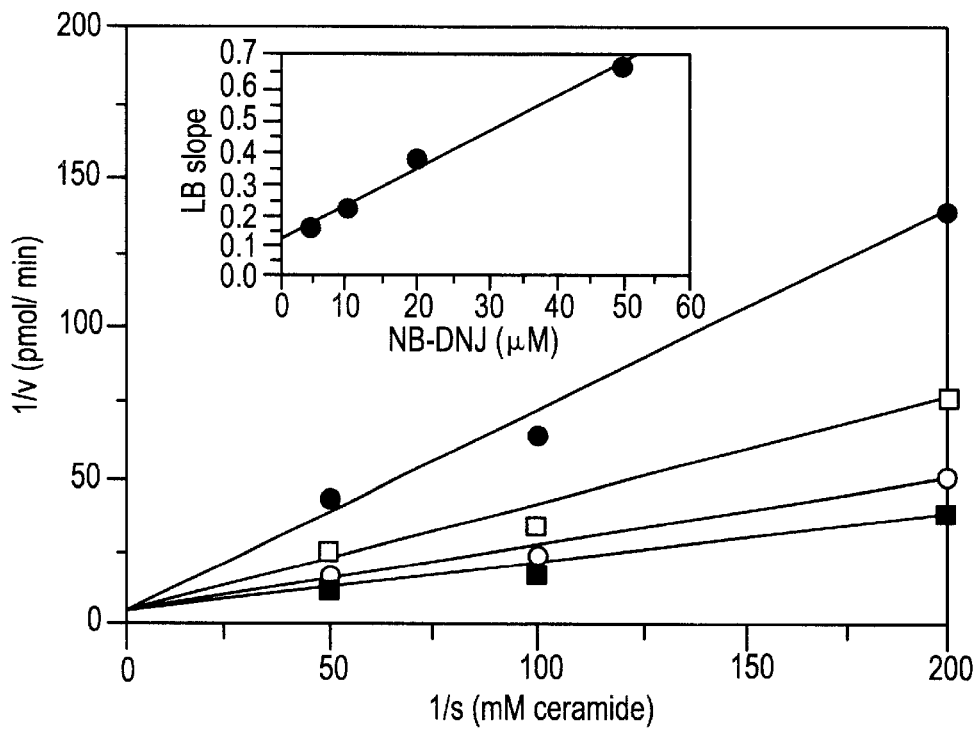
Figure 2B:
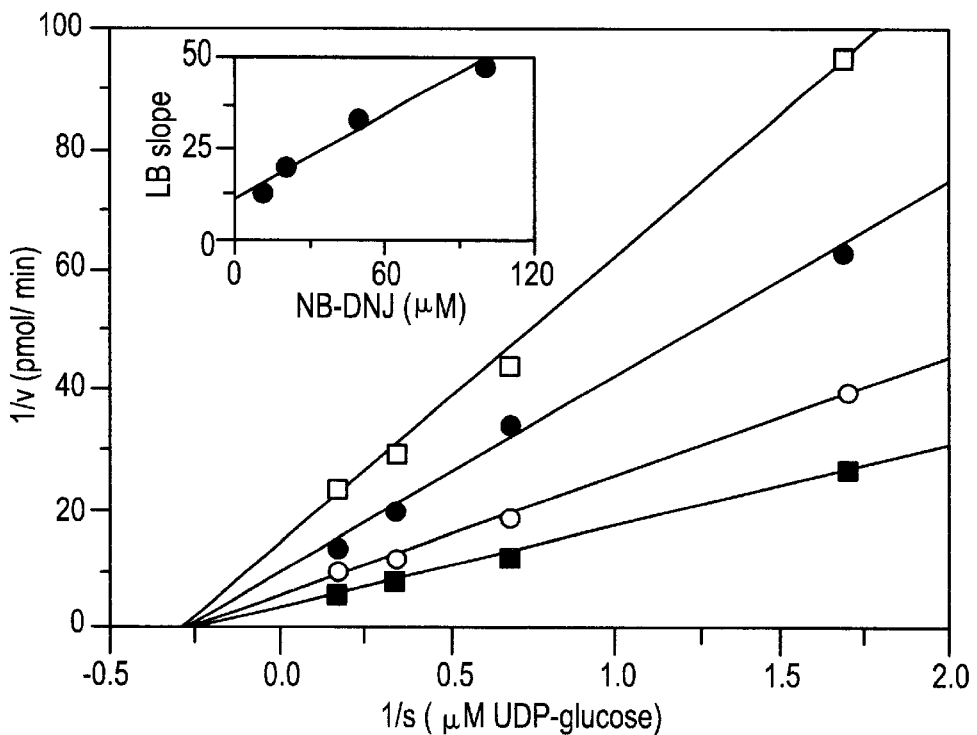

FIG. 2, in two parts, FIG. 2a and FIG. 2b, shows double reciprocal plots of the inhibition of the ceramide glucosyltransferase by N-butyl-DNJ (NB-DNJ). HL-60 cell ceramide glucosyltransferase activity was measured using ceramide concentrations of 5–20 $\mu$M (FIG. 2a) and UDP-glucose concentrations of 0.59–5.9 $\mu$M (FIG. 2b). NB-DNJ concentrations of 5–100 $\mu$M were used. The inhibition constants ($K_i$) were calculated by plotting the Lineweaver-Burk slope against inhibitor concentration as shown in the inserts.

Figure 3:
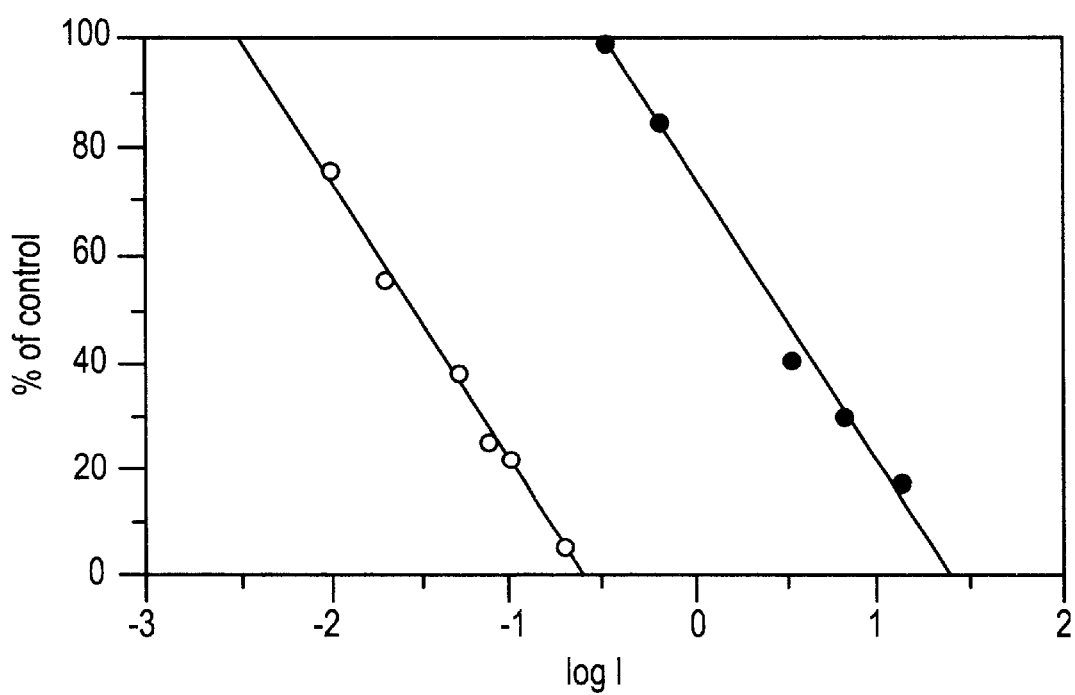

FIG. 3 shows inhibition of HL-60 cell ceramide glucosyltransferase activity by N-butyl-DNJ (open circles) and N-nonyl-DNJ (closed circles). Activity was expressed as a percentage of control without inhibitor and the $IC_{50}$ values calculated from the rate curves shown. N-butyl-DNJ=27.1 $\mu$M; N-nonyl-DNJ=2.8 $\mu$M.

FIG. 4 shows structural relationship between NB-DNJ and ceramide glucosyltransferase substrate.

(a) Ceramide structure from the crystal structure of glucosylceramide. The acceptor hydroxyl is on $C1^1$.

(b) The structure NB-DNJ (N-alkyl) based on NMR studies and molecular modelling.

(c) One possible overlay of ceramide and NB-DNJ.

Figure 5A:
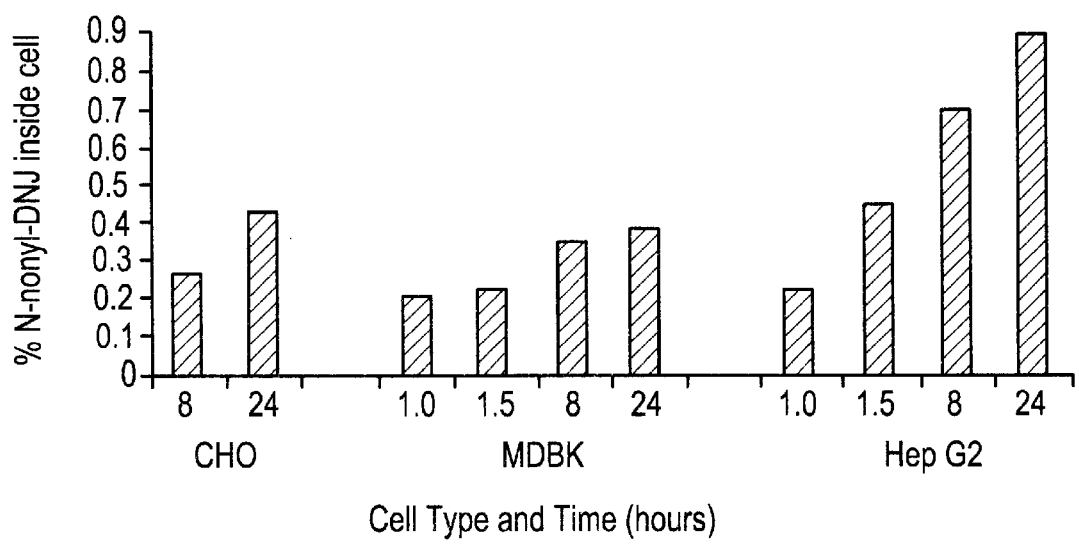
Figure 5B:
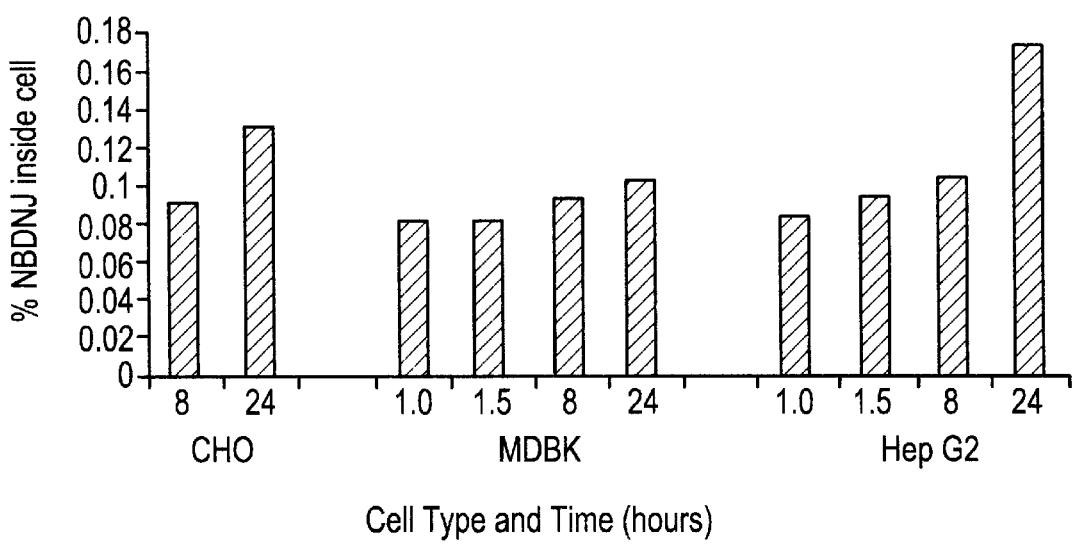

FIG. 5, in two parts, FIG. 5A and FIG. 5B, shows bar graphs of estimated radioactivity. Radiolabelled N-butyl-DNJ (FIG. 5B) and N-nonyl-DNJ (FIG. 5A) were added to cultured CHO, MDBK and HepG2 cells for the times indicated. Cells were extensively washed and acid precipitated. After solution in NaOH, cell associated radioactivity was determined as a percentage of radiolabelled compound added.

Figure 6:
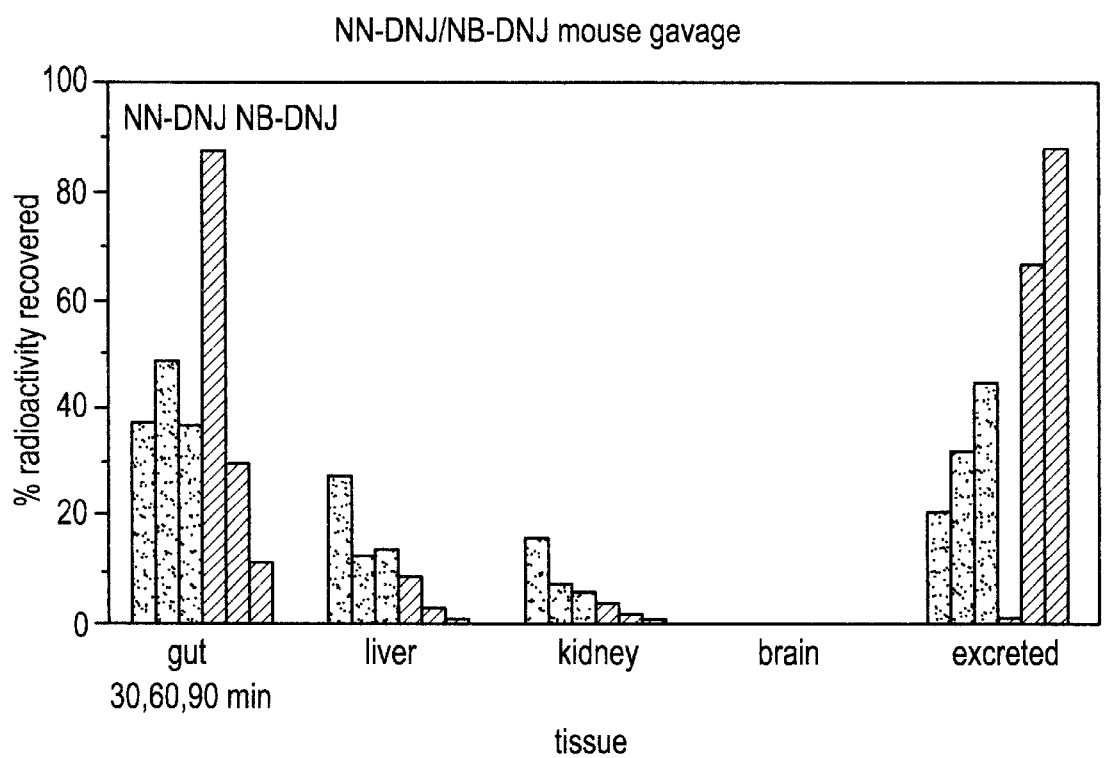

FIG. 6 is a bar graph which shows organ distribution of radiolabelled N-butyl-DNJ (NB-DNJ) and N-nonyl-DNJ (NN-DNJ). Mouse body fluids and organs were collected for different times after gavage with radiolabelled compound. Radioactivity in each sample was determined and expressed as a percentage of radio-activity recovered. Solid bars, NN-DNJ, hatched bars, NB-DNJ.

Figure 7:
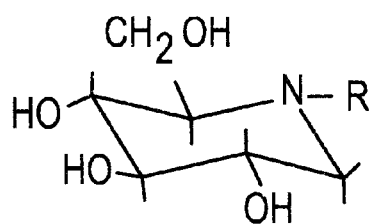

FIG. 7 shows the structures of N-alkylated deoxynojirimycin exemplified herein. Note that the C16 and C18 N-alkyl chains contain an unsaturated bond at ten and twelve carbon atoms from the nitrogen, respectively, whereas the others are saturated.

Figure 8:
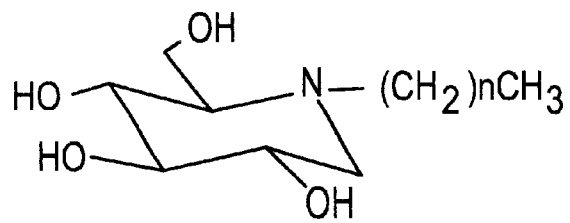

FIG. 8 shows Inhibitory Constants of C4 to C18 DNJ Analogs for Ceramide Glucosyltransferase and α-Glucosidase. FIG. 8 contains additional data to those seen in FIG. 3 showing inhibition constants ($IC_{50}$, $\mu M$) for the N-alkyl series measured against ceramide glucosyltransferase (CerGlcT) and α-glucosidase. The trend is similar to the FIG. 3 description - increasing chain length increases inhibition for glucosyltransferase, but not for glucosidase.

Figure 9:
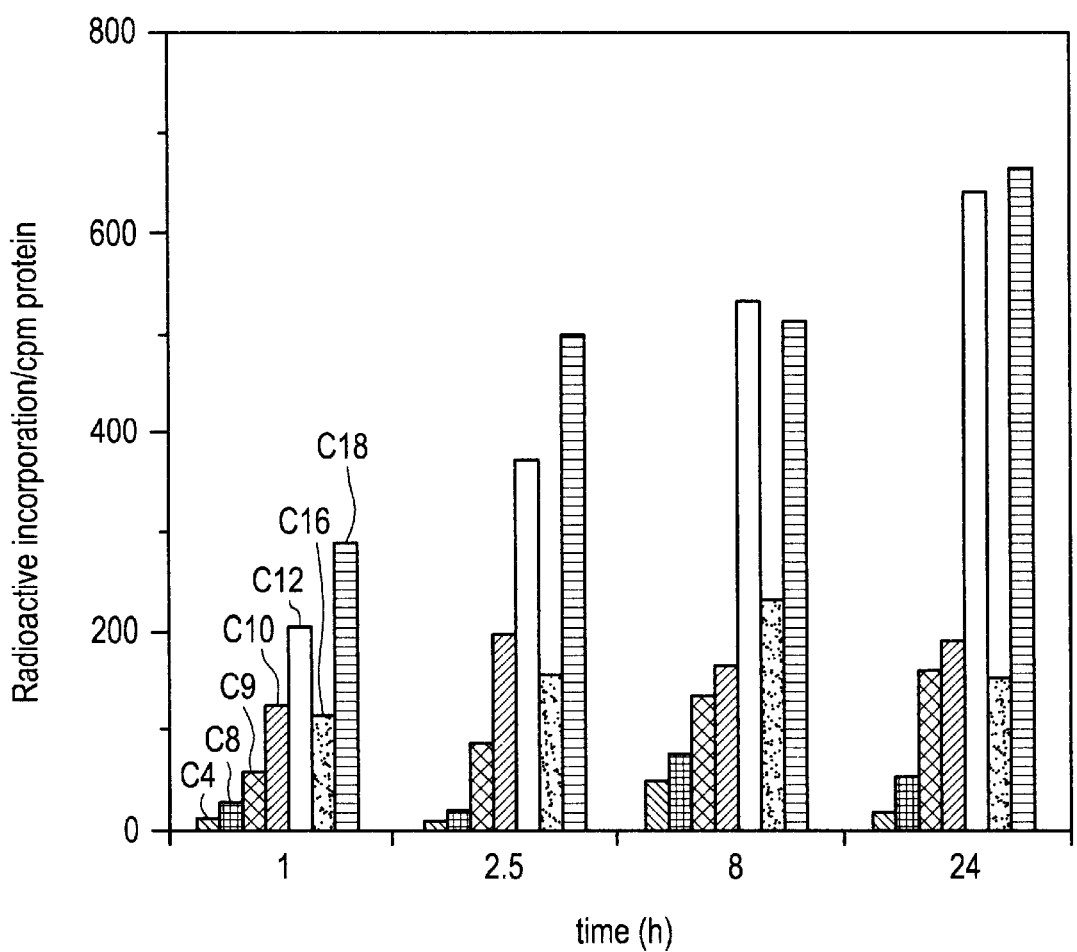

FIG. 9 shows C4 to C18 DNJ Analog Uptake in MBDK Cells in which radioactivity incorporation/cpm protein is plotted against time in hours (h). FIG. 9 shows additional data to those shown in FIG. 5 using C4–C18 N-alkylated DNJ compounds. Trend is apparent - increasing chain length increases cellular uptake in a time-dependent fashion. The double bond has some effect here since the unsaturated C16 and C18 analogs show similar kinetics to the fully saturated C10 and C12 analogs, respectively.

Figure 10:
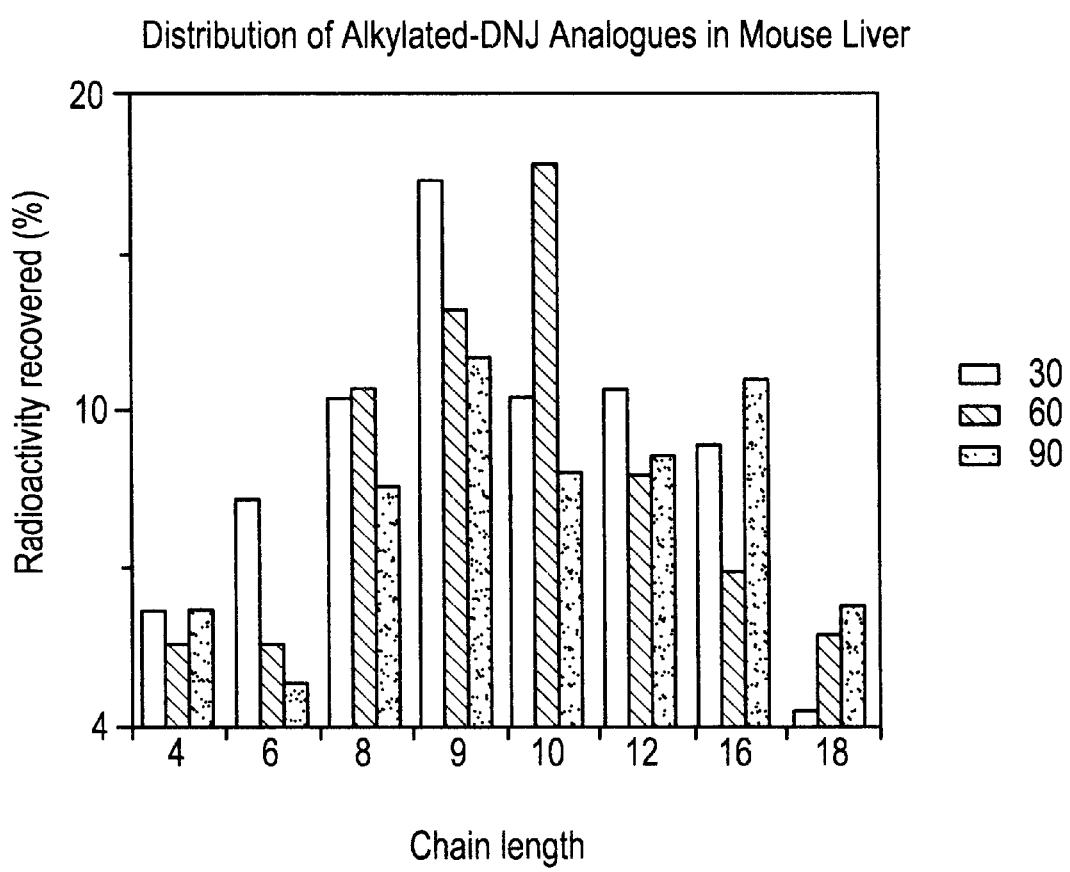

FIG. 10 shows Distribution of N-Alkylated DNJ Analogs in Mouse Liver. The radioactivity recovered (%) is plotted against N-alkyl chain length (C4 to C18) for 30 minutes (clear bars), 60 minutes (shaded bars) and 90 minutes (filled, black bars). FIG. 10 shows the results of oral gavage with radiolabelled N-alkylated compounds using methods described in FIG. 6. Short chain compounds (C4–C6) are rapidly cleared in a time-dependent manner. The C9 and C10 compounds show increased deposition and slower clearance. The C12 to C18 analogs show the reverse trend, i.e., reduced appearance in the liver but this increases with time.

Figure 11:
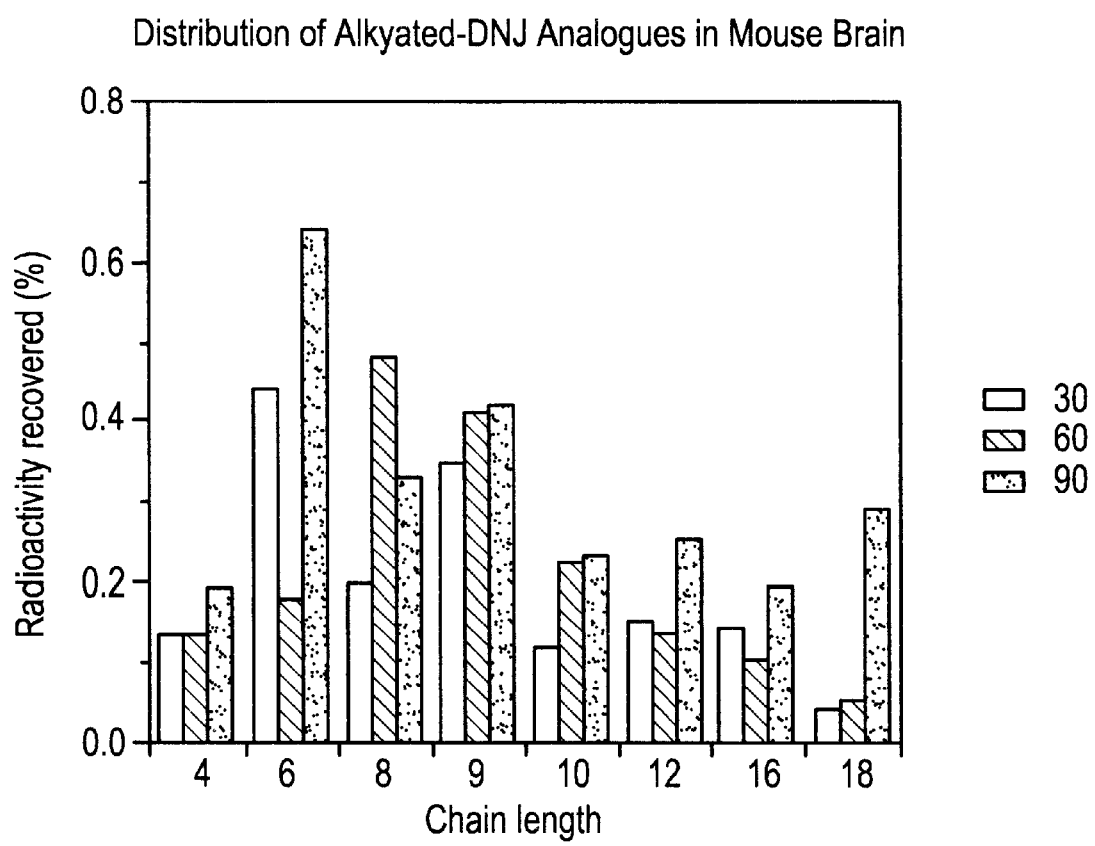
Figure 12A:
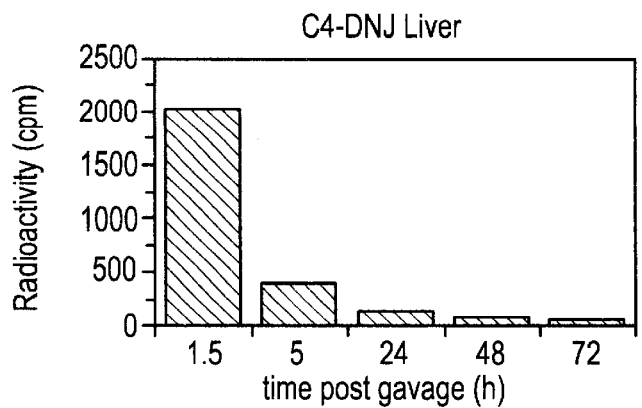
Figure 12B:
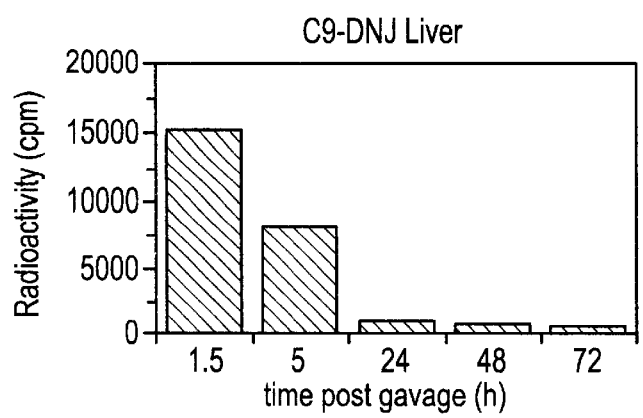
Figure 12C:
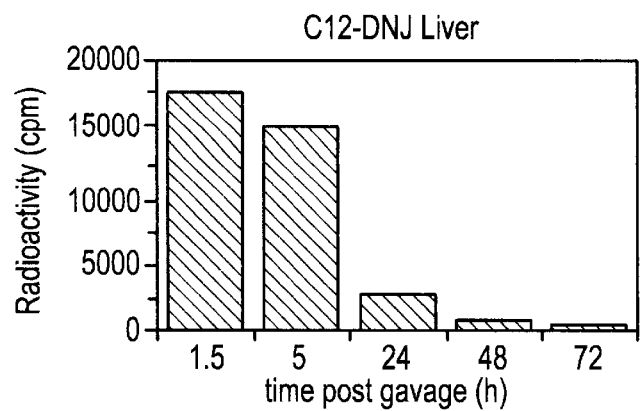
Figure 12D:
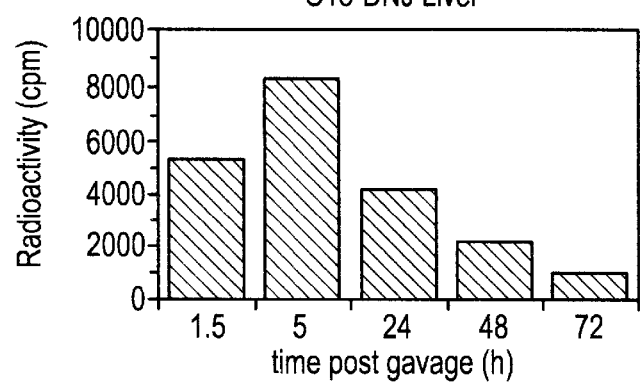
Figure 13A:
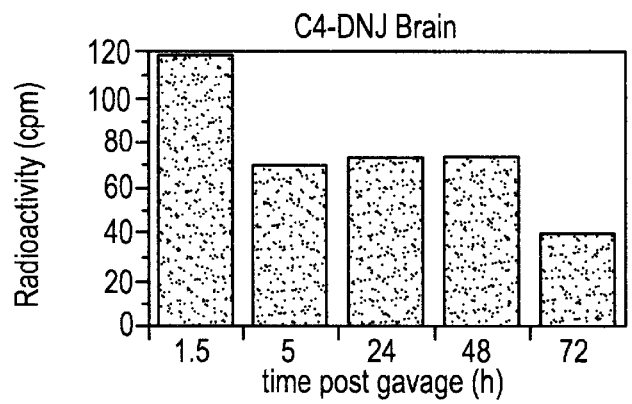
Figure 13B:
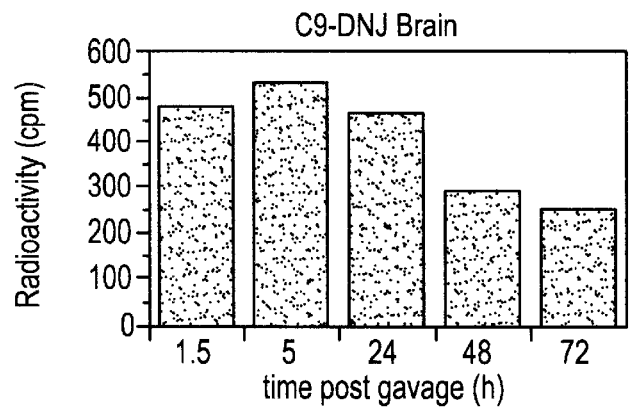
Figure 13C:
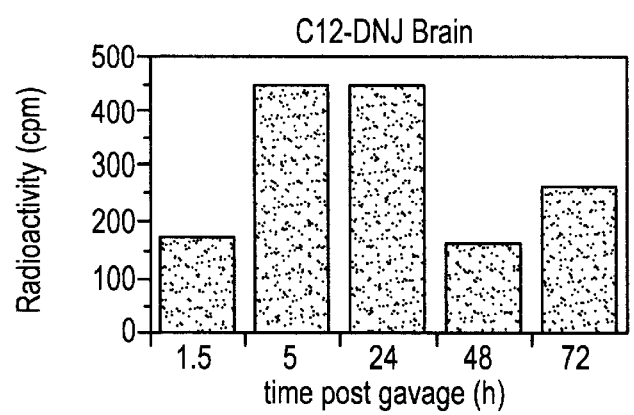
Figure 13D:
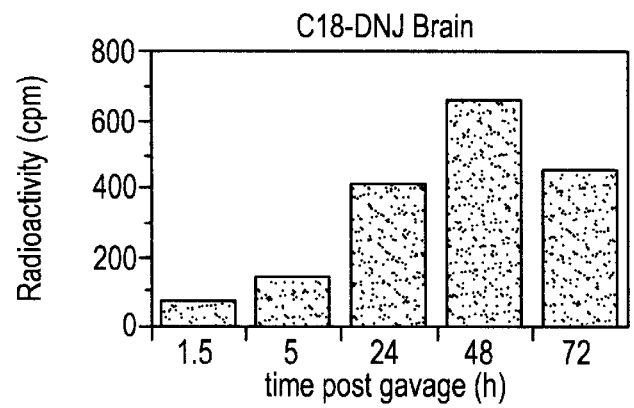

FIG. 11 shows Distribution of N-alkylated DNJ Analogs in Mouse Brain. The radioactivity recovered (%) is plotted against N-alkyl chain length (C4 to C18) for 30 minutes (clear bars), 60 minutes (shaded bars) and 90 minutes (filled, black bars). FIG. 11 shows that the progressive accumulation that is also seen in the brain has slowed kinetics suggesting that there is reduced adsorption of longer alkyl chain compounds from the gut.

FIG. 12 is a series of four bar charts, A, B, C and D, in which radioactivity (cpm) found in the liver is plotted against time post gavage in hours (h) with four different N-alkyl analogs of deoxynojirimycin (DNJ). The four analogs shown are:; FIG. 12A, N-butyl(C4); FIG. 12B, N-nonyl (C9); FIG. 12C, N-dodecyl(C12); FIG. 12D, N-cis-13-octadecenyl (C18). FIG. 12 shows that in the liver the majority of radioactive C4 is found after 1.5 h but with increasing chain length the clearance time is gradually increased with C18 showing significant deposition at 24 h post gavage.

FIG. 13 is a series of four bar charts, A, B, C and D, in which radioactivity (cpm) found in the brain is plotted against time post gavage in hours (h) with the same analog compounds as in FIG. 12. The four analogs shown are: FIG. 13A, N-butyl (C4); FIG. 13B, N-nonyl (C9); FIG. 13C, N-dodecyl (C12); FIG. 13D, N-cis-13-octadecenyl (C18). FIG. 13 shows that the same effect as in the liver in FIG. 12 is seen in the brain but at much longer time points, reflecting reduced transmission from the gut to blood and hence, brain.

Figure 14:
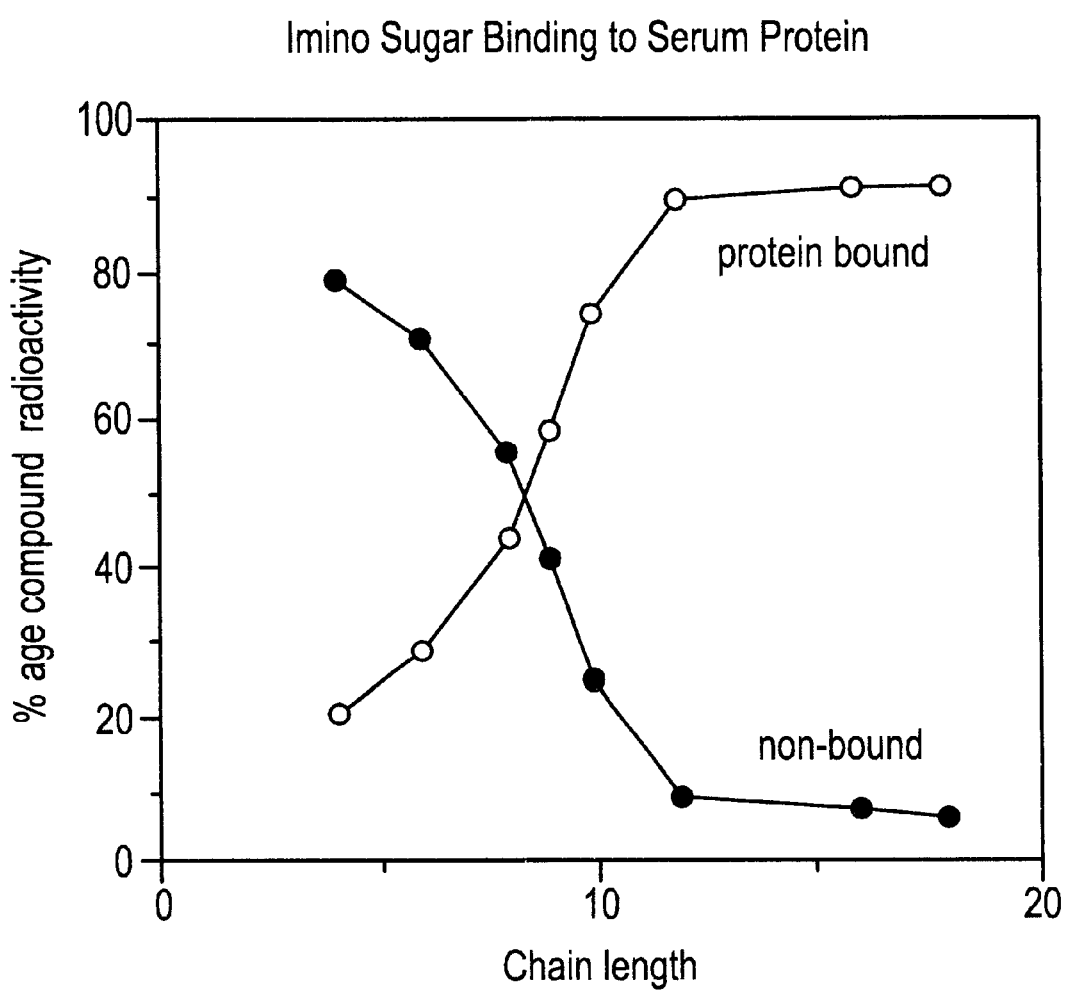

FIG. 14 shows Imino Sugar (N-alkyl DNJ) Binding to Serum Protein. The percentage compound radioactivity is plotted against N-alkyl chain length (C4 to C18) with the protein bound percentage shown by open circles and the non-bound percentage shown by filled circles. FIG. 14 shows the protein binding capacity of N-alkylated compounds. Short chain compounds (C4–C6) bind poorly but those larger than C10 are almost completely bound to protein. The C8 and C9 analogs appear to favor equally, protein and solution phase.

In order to illustrate the invention in greater detail, the following specific laboratory examples were carried out. Although specific examples are thus illustrated herein, it will be appreciated that the invention is not limited to these specific, illustrative examples or the details therein.

EXAMPLE I

A comparison was made between N-butyl-DNJ and N-nonyl-DNJ for glycolipid biosynthesis inhibition which showed that potency is cell and chain length dependent. Chinese Hamster Ovary (CHO) cells and human myeloid (HL-60) cells grown in the presence of varying concentrations of inhibitor in addition to a precursor (radiolabelled palmitic acid) of glycolipid biosynthesis were treated with solvents to extract the glycolipids by the procedure described by Platt et al., *J. Biol. Chem.* 269, 8362–8365 (1994).

The radiolabelled lipids were separated by TLC (FIG. 1) and bands corresponding to glucosylceramide and lactosylceramide were quantitated by scanning densitometry to estimate the reduction in glycolipid biosynthesis. These data were plotted to obtain inhibitory constants ($IC_{50}$) for both cell lines and compounds (Table 1).

These data show that cell lines have different sensi-tivities to both N-butyl- and N-nonyl-DNJ. HL-60 cells are more than 10 times more sensitive to N-butyl-DNJ and 100 times more sensitive to N-nonyl-DNJ than CHO cells. This cell specificity is unexpected. In addition, N-nonyl is between 10 and 365 times more effective than N-butyl-DNJ.

Detailed work to probe the mechanism of the ceramide glucosyltransferase, the enzyme inhibited by alkylated deoxynojirimycin compounds has demonstrated that these compounds are competitive inhibitors for ceramide and non-competitive inhibitors for UDP-glucose (FIG. 2). N-nonyl-DNJ has a 10-fold increased potency over N-butyl-DNJ in inhibiting ceramide glucosyltransferase in in vitro assays ($IC_{50}$ values of 2.8 $\mu M$ and 27.1 $\mu M$ respectively, see FIG. 3).

The mechanism of action of alkylated deoxynojirimycin compounds is proposed to be that of ceramide mimicry and a model demonstrating this mimicry at the molecular level is shown in FIG. 4. An energy minimized molecular model of NB-DNJ and ceramide predicts structural homology of three chiral centers and the N-alkyl chain of NB-DNJ, with the trans-alkenyl and N-acyl chain of ceramide. This increased in vitro potency does not explain the dramatic difference in inhibition of glycolipid biosynthesis in cellular systems.

The activity is explained by the differential uptake into cells. In three cell lines, CHO, MDBK and HepG2, radiolabelled N-nonyl-DNJ and N-butyl-DNJ were incubated for up to 24 hours and the amount of cell-associated radioactivity determined. In all cases N-nonyl-DNJ was increased by 3.5–5 fold. It is clearly the combination of the inhibitory effect and increased uptake that is important in potentiating the inhibition by N-nonyl-DNJ.

Further evidence that longer alkyl chains are taken up much better has been obtained by in vivo studies with mouse. After oral gavage with radiolabelled N-nonyl-DNJ and N-butyl-DNJ for 30, 60, and 90 minutes, the body fluids were collected and organs removed for estimations of radio activity (FIG. 5). The amount of radioactivity recovered in the liver and brain was 10 fold higher for N-nonyl-DNJ than N-butyl-DNJ after 90 min (see Table 2).

Evidence was obtained that longer (than C9) chain DNJ compounds are more effective ceramide glucosyltransferase inhibitors. This follows from proposed mechanism of action studies that demonstrate enhanced potency correlates with ceramide mimicry (FIG. 4). More specifically, N-decyl-DNJ (C10) shows inhibition at 50 times lower concentrations than N-butyl-DNJ in the HL-60 cell-based assay described above. In view of the above data, the long-chain N-alkyl derivatives of DNJ are effective for treatment of glycolipid storage diseases.

TABLE 1

Inhibition of glycolipids of N-butyl- and N-nonyl-DNJ. Radiolabelled glucosylceramide and lactosylceramide bands from FIG. 1 were quantitated by scanning densitometry and the percentage of control (no treatment, track a, FIG. 1) expressed in comparison to compound dose. From the linear curve, an $IC_{50}$ value was obtained. A range of values is quoted to represent variability of the radiolabelled products.

| Cells | N-butyl-DNJ ($IC_{50}$, μM) | N-nonyl-DNJ ($IC_{50}$, μM) |
|---|---|---|
| CHO | 25–50 | 2–2.7 |
| HL-60 | 1.8–7.3 | 0.02–0.4 |

TABLE 2

Recovery of radiolabelled compounds after administration in the normal mouse. Mouse body fluids and organs were collected for different times after gavage with radiolabelled compound. Radioactivity in each sample was determined and expressed as a percentage of radioactivity recovered (data from FIG. 5).

| | % recovered N-nonyl-DNJ | | % recovered N-butyl-DNJ | |
|---|---|---|---|---|
| Time (min) | Liver | Brain | Liver | Brain |
| 30 | 27.1 | 0.4 | 8.5 | 0.2 |
| 60 | 12.6 | 0.3 | 2.8 | 0.1 |
| 90 | 13.5 | 0.4 | 0.9 | 0.03 |

EXAMPLE II

The laboratory procedures of Example I were carried out to further demonstrate the advantage of the long-chain N-alkyl derivatives of deoxynojirimycin compared to the short-chain analogs for the treatment of glycolipid storage diseases. The chemical structures of the analogs compared in this Example are shown in FIG. 7. These analogs are saturated except the C16 and C18 alkyl chain analogs which are mono-unsaturated.

The inhibition constants ($IC_{50}$) for the N-alkyl series measured against ceramide glycosyltransferase (CerGlcT) and alpha-glucosidase are shown in FIG. 8. The trend is similar to that shown in FIG. 3 in which increasing chain length increases inhibition for glycosyltransferase, but not for glucosidase. This supports the mechanism of ceramide mimicry as the basis of inhibition shown in FIG. 4. The optimal chains length appears to be C10 (decyl).

FIG. 9 confirms the trend shown in FIG. 5 in which increasing chain length increases cellular uptake in a time dependent manner. The effect of the double bond in the C16 and C18 analogs is seen in that the C16 shows similar kinetics to the saturated C10 analog, and the C18 shows similar kinetics to the saturated C12 analog.

In FIG. 10, the results of oral gavage with radiolabelled analogs as in FIG. 6 are shown for additional analogs. Short-chain analogs (C4 to C6) are cleared rapidly in a time dependent manner. The C9 and C10 analogs show increased deposition and slower clearance. The C12 to C18 analogs show reduced appearance in the liver, but this increases with time. These results support the mechanism of increased tissue uptake by longer alkyl chain analogs since after 30 minutes the accumulation in the liver of the C9 analog is ten times that seen with the short-chain C4 analog.

FIG. 11 shows the progressive accumulation that is also seen in the mouse brain has slowed kinetics and thereby suggests that there is a reduced adsorption of the longer chain alkyl analogs from the gut.

Further evidence of reduced adsorption is shown in FIGS. 12 and 13 when longer time points post gavage are used to monitor tissue deposition. Thus, FIG. 12 shows that in the liver the majority of radioactive C4 is found after 1.5 hours, but with increasing chain length the clearance time is gradually increased, with C18 showing significant deposition at 24 hours post gavage. FIG. 13 shows that the same effect is seen in the mouse brain but at much longer time points, reflecting reduced transmission from the gut to the blood and hence the brain.

FIG. 14 shows the protein binding capacity of the N-alkylated analogs of deoxynojirimycin. The short-chain analogs (C4 to C6) bind poorly but those larger than C10 are almost completely bound to protein. The C8 and C9 analogs appear to favor equally, protein and solution phase.

In summary then, the slowed uptake from the gut by the long-chain alkyl analogs of deoxynojirimycin shown in Example II results in slowed transmission to the liver but there is progressive accumulation. This accumulation in the liver with time is also shown in the brain. These results have great significance for the treatment of glycolipid storage diseases, especially when the storage in the brain shows pathology for Gaucher type II/III, Tay-Sachs and Sandhoff diseases.

Various other examples will be apparent to the person skilled in the art after reading the present disclosure without departing from the spirit and scope of the invention. It is intended that all such other examples be included within the scope of the appended claims.

What is claimed is:

1. The method of treating a patient affected with a glycolipid storage disease characterized by the synthesis of glucosylceramide by glucosyltransferase in the biosynthesis of glycosphingolipid comprising administering to said patient a long-chain N-alkyl derivative of deoxynojirimycin having from nine to about twenty carbon atoms in the alkyl chain in an amount effective for alleviating or inhibiting said glycolipid storage disease.

2. The method of claim 1 in which the long-chain N-alkyl derivative of deoxynojirimycin is N-nonyl-DNJ or N-decyl-DNJ.

3. The method of claim 2 in which the N-alkyl derivative of deoxynojirimycin is N-nonyl-DNJ.

4. The method of treating a patient affected with Gaucher's disease comprising administering to said patient a long-chain N-alkyl derivative of deoxynojirimycin having from nine to about twenty carbon atoms in the alkyl chain in an amount effective for alleviating or inhibiting said Gaucher's disease.

5. The method of claim 4 in which the long-chain N-alkyl derivative of deoxynojirimycin is N-nonyl-DNJ or N-decyl-DNJ.

6. The method of claim 5 in which the N-alkyl derivative of deoxynojirimycin is N-nonyl-DNJ.

7. The method of claim 1 in which the N-alkyl derivative of deoxynojirimycin is administered in a dosage of from about 0.1 to about 1000 mg in a pharmaceutically acceptable diluent or carrier.

8. The method of claim 2 in which the N-nonyl-DNJxor N-decyl-DNJ is administered in a dosage of from about 0.1 to about 1000 mg in a pharmaceutically acceptable diluent or carrier.

9. The method of claim 3 in which the N-nonyl-DNJ is istered in a dosage of from about 0.1 to about 1000 mg in rmaceutically acceptable diluent or carrier.

10. The method of claim 4 in which the N-alkyl derivative oxynojirimycin is administered in a dosage of from about 0.1 out 1000 mg in a pharmaceutically acceptable diluent or carrier.

11. The method of claim 5 in which the N-nonyl-DNJ or N-DNJ is administered in a dosage of from about 0.1 to about mg in a pharmaceutically acceptable diluent or carrier.

12. The method of claim 6 in which the N-nonyl-DNJ is istered in a dosage of from about 0.1 to about 1000 mg in rmaceutically acceptable diluent or carrier.

* * * * *

UNITED STATES PATENT AND TRADEMARK OFFICE
CERTIFICATE OF CORRECTION

PATENT NO. : 6,610,703 B1
DATED : August 26, 2003
INVENTOR(S) : Gary S. Jacob et al.

It is certified that error appears in the above-identified patent and that said Letters Patent is hereby corrected as shown below:

Column 2,
Lines 15-16, "N-non erivative" should read -- N-nonyl derivative --.

Column 10,
Line 5, "DNJxor" should read -- DNJ or --;
Line 10, "istered" should read -- administered --;
Line 11, "rmaceutically" should read -- a pharmaceutically --;
Line 13, "oxynojirimycin" should read -- of deoxynojirimycin --;
Line 17, "N-DNJ" should read -- N-decyl-DNJ --;
Line 18, "about mg" should read -- about 1000 mg --;
Line 20, "istered" should read -- administered --;
Line 21, "rmaceutically" should read -- a pharmaceutically --.

Signed and Sealed this

Eighth Day of June, 2004

JON W. DUDAS
*Acting Director of the United States Patent and Trademark Office*